US009988781B2

(12) United States Patent
Pickover et al.

(10) Patent No.: US 9,988,781 B2
(45) Date of Patent: Jun. 5, 2018

(54) SAND CLEANING VEHICLE AND A METHOD OF CLEANING SAND USING THE SAME

(71) Applicant: INTERNATIONAL BUSINESS MACHINES CORPORATION, Armonk, NY (US)

(72) Inventors: Clifford A. Pickover, Yorktown Heights, NY (US); Maja Vukovic, New York, NY (US); Komminist Weldemariam, Nairobi (KE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days. days.

(21) Appl. No.: 15/273,350

(22) Filed: Sep. 22, 2016

(65) Prior Publication Data

US 2018/0080188 A1   Mar. 22, 2018

(51) Int. Cl.
| | | |
|---|---|---|
| *B07B 1/49* | (2006.01) | |
| *E01H 12/00* | (2006.01) | |
| *B07C 5/34* | (2006.01) | |
| *A61L 2/18* | (2006.01) | |
| *A61L 2/10* | (2006.01) | |

(Continued)

(52) U.S. Cl.
CPC .............. *E01H 12/002* (2013.01); *A61L 2/10* (2013.01); *A61L 2/18* (2013.01); *B07C 5/34* (2013.01); *G01S 19/42* (2013.01); *G06F 17/30864* (2013.01); *A61L 2202/11* (2013.01); *A61L 2202/15* (2013.01); *A61L 2202/16* (2013.01)

(58) Field of Classification Search
CPC .......... E01H 12/00; E01H 12/002; B07C 5/34
USPC ................................... 209/420, 421
See application file for complete search history.

(56) References Cited

U.S. PATENT DOCUMENTS 4,205,624 A * 6/1980 Yacus ...................... A01K 1/01
                                                            119/174
5,133,413 A * 7/1992 Baxter ..................... E01H 12/00
                                                            15/84

(Continued)

FOREIGN PATENT DOCUMENTS

CN      201485814        5/2010
DE      2903205 A1 *     8/1980      ............. E01H 12/00

(Continued)

OTHER PUBLICATIONS

Kara S. Doran, et al., A Method of Determining Average Beach Slope and Beach Slope Variability for U.S. Sandy Coastlines, USGS Open File Report 2015-0153, 10 pages https://pubs.usgs.gov/of/2015/1053/pdf/ofr2015-1053.pdf (last visited Sep. 22, 2016).

(Continued)

*Primary Examiner* — Terrell H Matthews
(74) *Attorney, Agent, or Firm* — F. Chau & Associates, LLC (57) ABSTRACT

A sand cleaning vehicle including a debris collection mechanism that collects debris from sand, a storage compartment that stores the collected debris, a capture device that captures at least one image of the collected debris, a memory storing a computer program, and a processor that executes the computer program. The computer program categorizes the collected debris into a plurality of different debris types using at least one image of the collected debris.

18 Claims, 5 Drawing Sheets

(51) Int. Cl.
*G01S 19/42* (2010.01)
*G06F 17/30* (2006.01)

(56) References Cited

U.S. PATENT DOCUMENTS

| | | | | |
|---|---|---|---|---|
| 5,192,435 | A * | 3/1993 | Francisco, Jr. | B01D 33/04 15/340.1 |
| 6,735,327 | B1 * | 5/2004 | Shofner | D01G 31/003 382/111 |
| 7,145,695 | B2 * | 12/2006 | Endo | G06F 17/30256 358/2.1 |
| 7,870,042 | B2 * | 1/2011 | Maruca | G06Q 10/087 209/509 |
| 8,139,109 | B2 * | 3/2012 | Schmiedel | G01S 17/023 348/118 |
| 8,330,059 | B2 * | 12/2012 | Curotto | G06Q 10/30 177/136 |
| 8,464,874 | B2 * | 6/2013 | Whitley | E01H 12/002 171/111 |
| 8,674,243 | B2 * | 3/2014 | Curotto | G06Q 10/30 177/136 |
| 2003/0031543 | A1 * | 2/2003 | Elbrink | B65F 3/02 414/408 |
| 2009/0229234 | A1 * | 9/2009 | Ettrich | A01G 1/125 56/13.1 |
| 2012/0046203 | A1 * | 2/2012 | Walsh | A61B 5/157 506/39 |
| 2014/0379588 | A1 * | 12/2014 | Gates | G06Q 10/0631 705/308 |
| 2015/0224544 | A1 * | 8/2015 | McGloughlin | B07C 5/342 209/577 |
| 2015/0283586 | A1 * | 10/2015 | Dante | A24B 3/16 209/577 |
| 2016/0158817 | A1 * | 6/2016 | Zediker | C10G 75/00 134/1 |

FOREIGN PATENT DOCUMENTS

| | | | | |
|---|---|---|---|---|
| DE | 2903205 | A1 * | 8/1980 | E01H 12/00 |
| EP | 0 277 739 | | 8/1988 | |
| EP | 0 480 074 | | 4/1992 | |
| FR | 2661700 | A1 * | 11/1991 | B07B 9/00 |
| FR | 2661700 | A1 * | 11/1991 | B07B 9/00 |
| WO | WO 9010754 | A1 * | 9/1990 | E01H 1/042 |
| WO | WO-9010754 | A1 * | 9/1990 | E01H 1/042 |

OTHER PUBLICATIONS

33 CFR Part 328—Definition of Waters of the United States, 3 pages http://www.nap.usace.army.mil/Portals/39/docs/regulatory/regs/33cfr328.pdf (last visited Sep. 22, 2016).

Soren Goyal, et al., Object Recognition Using Deep Neural Networks: A Survey, arXiv.org. Dec. 2014, http://arvix.org/abs/1412.3684 (last visited Sep. 22, 2016).

Beach Cleaner Informational Resource, Balancing Environmental Concerns with Beach Attractiveness, Feb. 15, 2012, http://beachcleaner.com/beach-cleaner-blog/balancing-environmental-concerns-with-beach-attractiveness#sthash.iAhVfab1.dpuf (last visited Sep. 22, 2016).

Unesco, Environment and Development in Coastal Regions and in Small Islands, Beach Debris (7), http://www.unesco.org/csi/pub/papers3/sande9.htm (last visited Sep. 22, 2016).

Wikipedia, Sand Cleaning Machine https://en.wikipedia.org/Sand_cleaning_machine (last visited Sep. 22, 2016).

* cited by examiner

SAND CLEANING VEHICLE AND A METHOD OF CLEANING SAND USING THE SAME

BACKGROUND

Exemplary embodiments of the present invention relate to a sand cleaning vehicle and a method of cleaning sand using the same.

A sand cleaning vehicle is a machine that removes debris or other foreign matter from sand by, for example, dragging a raking or sifting device over the sand. The sand cleaning vehicle can be pulled by a motor vehicle, such as a quad-bike or tractor, or self-pulled on tracks or wheels. The sand cleaning vehicle collects sand by utilizing a scooping or dragging mechanism and subsequently rakes or sifts out the debris or foreign matter, which is then placed in a collecting tray located in the sand cleaning vehicle.

Sand cleaning vehicles are used by seaside communities to remove trash left by beach visitors and other pollution that has accumulated on beaches. Sand cleaning vehicles not only provide for the improvement of beach aesthetics, but are also important for human safety and environmental preservation. Sand cleaning vehicles remove sharp objects, such as syringes, that are harmful to humans as well as other pollution that may be harmful to marine life through entanglement or ingestion. Sand cleaning vehicles can also be used in the removal of dead fish prior to their release of toxins into the air, sand, and water. After oil spill disasters, sand cleaning vehicles have been effectively implemented to remove tar balls and oil from the sand. Sand cleaning vehicles can be used on other terrains besides beaches, such as sand fields, beach volleyball courts, and playgrounds.

SUMMARY

Exemplary embodiments of the present invention provide a sand cleaning vehicle. The sand cleaning vehicle includes a debris collection mechanism that collects debris from sand, a storage compartment that stores the collected debris, a capture device that captures at least one image of the collected debris, a memory storing a computer program, and a processor that executes the computer program. The computer program categorizes the collected debris into a plurality of different debris types using at least one image of the collected debris.

According to an exemplary embodiment of the present invention, the sand cleaning vehicle may further include a network adapter. The network adapter may establish a network connection with a remote computer, in which the computer program may transmit the at least one image of the collected debris via the network adapter to the remote computer.

According to an exemplary embodiment of the present invention, the computer program may categorize the collected debris into a plurality of debris types using a debris classification model received via the network adapter from the remote computer.

According to an exemplary embodiment of the present invention, the sand cleaning vehicle may further include a network adapter. The network adapter may establish a network connection with a remote computer, in which the computer program may generate an assessment report indicating the different debris types collected from the sand and may transmit the assessment report to the remote computer.

According to an exemplary embodiment of the present invention, the sand cleaning vehicle may further include a global positioning system (GPS) device. The GPS device may detect a current location of the sand cleaning vehicle. The computer program may create a map indicating locations at which the collected debris were collected using the at least one image of the collected debris and the current location of the sand cleaning vehicle.

According to an exemplary embodiment of the present invention, the sand cleaning vehicle may further include a network adapter. The network adapter may establish a network connection with a remote computer, in which the computer program transmits the map to the remote computer via the network adapter.

According to an exemplary embodiment of the present invention, the sand cleaning vehicle may further include a disinfecting mechanism, in which one of the different debris types represents hazardous debris. The disinfecting mechanism may disinfect the sand at a location at which debris categorized as the hazardous debris is collected. The sand may be disinfected while it is located within the sand cleaning vehicle or on ground below the sand cleaning vehicle.

According to an exemplary embodiment of the present invention, the disinfecting mechanism may include one of an ultraviolet (UV) light disinfecting mechanism that irradiates the sand with UV light, and a disinfectant spraying mechanism that sprays the sand with a disinfectant spray.

The sand cleaning vehicle may further include a global positioning system (GPS) device and a network adapter. The GPS device may detect a current location of the sand cleaning vehicle. The network adapter may establish a network connection with a remote computer. The computer program may track the current location of the sand cleaning vehicle during at least one sand cleaning outing The computer program may further identify a high tide line on a beach during the at least one sand cleaning outing. The high tide line may correspond to a continuous physical marking identified by the capture device that indicates a portion of the beach furthest from an ocean that is reached by a rising tide. The computer program may further record locations at which each piece of the collected debris is collected and locations corresponding to the high tide line. The computer program may determine a relationship between the locations at which each piece of the collected debris is collected and the locations corresponding to the high tide line. The computer program may transmit a report. The report may indicate the determined relationship to the remote computer via the network adapter.

The sand cleaning vehicle may further include a global positioning system (GPS) device and a network adapter. The GPS device may detect a current location of the sand cleaning vehicle. The network adapter may establish a network connection with a remote computer. The computer program may track a current location of the sand cleaning vehicle during at least one sand cleaning outing. The computer program may further determine a slope of a beach at a first plurality of locations during the at least one sand cleaning outing. The computer program may record a first plurality of locations and the corresponding slope, and a second plurality of locations at which each piece of the collected debris is collected. The computer program may determine a relationship between the slope of the beach and the second plurality of locations at which each piece of the collected debris was collected. The computer program may transmit a report. The report may indicate a location of the area having the high debris accrual rate and a location of the area having the low debris accrual rate to the remote computer via the network adapter.

According to an exemplary embodiment of the present invention, the sand cleaning vehicle may further include a sorting mechanism that sorts the collected debris. The storage compartment may include a plurality of sub-compartments. The sorting mechanism may separate the collected debris into the sub-compartments according to the different debris types.

According to an exemplary embodiment of the present invention, the sand cleaning vehicle may be an autonomous vehicle.

Exemplary embodiments of the present invention provide a method of cleaning sand. Debris is collected from the sand by a sand cleaning vehicle. At least one image of the collected debris is captured by a capture device disposed in the sand cleaning vehicle. The collected debris is stored in a storage compartment disposed in the sand cleaning vehicle. The collected debris is categorized into a plurality of different debris types using at least one image of the collected debris.

According to an exemplary embodiment of the present invention, the categorizing of the collected debris into the plurality of different debris types using the at least one image may include comparing at least one image to a plurality of images stored in the database. Each image stored in the database may belong to one of the different types of debris. The at least one image may be matched to one of the plurality of images in the database.

According to an exemplary embodiment of the present invention, the method may further include tracking a current location of the sand cleaning vehicle during at least one outing. A high tide line may be identified on a beach during the at least one sand cleaning outing. The high tide line may correspond to a continuous physical marking identified by the capture device that indicates a portion of the beach furthest from an ocean that is reachable by a rising ride. Locations at which each piece of the collected debris is collected and the locations corresponding to the high tide line may be recorded. A relationship between the locations at which each piece of the collected debris is collected and the locations corresponding to the high tide line may be determined. A future sand cleaning outing may be scheduled, such that the sand cleaning vehicle spends more time cleaning areas having a high debris accrual rate as indicated by the determined relationship than cleaning areas having a low debris accrual rate as indicated by the determined relationship during the future sand cleaning outing.

According to an exemplary embodiment of the present invention, the method may further include tracking a current location of the sand cleaning vehicle during at least one sand cleaning outing. A slope of a beach may be determined at a first plurality of locations during the at least one sand cleaning outing. The first plurality of locations and the corresponding slope, and a second plurality of locations at which each piece of the collected debris is collected may be recorded. A relationship between the slope of the beach and the second plurality of locations at which each piece of the collected debris was collected may be determined. A future sand cleaning outing may be scheduled such that such that the sand cleaning vehicle spends more time cleaning areas having a high debris accrual rate as indicated by the determined relationship than cleaning areas having a low debris accrual rate as indicated by the determined relationship during the future sand cleaning outing.

According to an exemplary embodiment of the present invention, the method may further include tracking a current location of the sand cleaning vehicle, during a plurality of sand cleaning outings, as the sand cleaning vehicle collects debris from the sand. A location may be recorded at which each piece of the collected debris was collected during each sand cleaning outing. An area may be identified having a high debris accrual rate and an area having a low debris accrual rate using the recorded locations. A future sand cleaning outing may be scheduling such that the sand cleaning vehicle spends more time cleaning the area having the high debris accrual rate than cleaning the area having the low debris accrual rate during the future sand cleaning outing.

According to an exemplary embodiment of the present invention, the method may further include transmitting the at least one image from the sand cleaning vehicle to at least one computer that is remotely located from the sand cleaning vehicle, in which the collected debris is categorized into the plurality of different debris types by the at least one computer.

According to an exemplary embodiment of the present invention, the method may further include transmitting the at least one image from the sand cleaning vehicle to the at least one computer in real-time.

According to an exemplary embodiment of the present invention, the method may further include generating an assessment report indicating the different debris types collected from the sand. The assessment report may be transmitted to at least one computer that is located remotely from the sand cleaning vehicle.

BRIEF DESCRIPTION OF THE DRAWINGS

The above and other features of the present invention will become more apparent by describing in detail exemplary embodiments thereof, with reference to the accompanying drawings, in which.

DETAILED DESCRIPTION OF THE EMBODIMENTS

Exemplary embodiments of the present Invention provide a sand cleaning vehicle and a method of cleaning sand using the same. The sand cleaning vehicle may utilize raking technology, sifting technology or a combination of raking and sifting technology. Raking technology may be used on dry or wet sand. Raking technology may include a raking machine with a rotating conveyor belt. The rotating conveyor belt may include tines that comb through the sand to pick up buried debris and surface debris while leaving the sand behind. Since the sand remains on the beach, sand cleaning vehicles using raking technology can move at high speeds. Sifting technology may be used on dry sand and soft terrain. Sifting technology may include collecting sand and debris through a pick-up blade included on the sand cleaning vehicle. The sand and debris may then be disposed on a vibrating screen belt which sifts the sand through holes. The debris may be disposed into a collecting tray usually located at the back of the sand cleaning vehicle. The size of the debris collected may be determined by the size of the holes in the vibrating screen belt. Since sand and debris are lifted onto the vibrating screen belt, time is needed to sift through the contents in order to collect the debris. A combination of raking and sifting technology may use rotating tines that scoop sand and debris onto the vibrating screen belt instead of solely using a pick-up blade. The position of the tines may be adjusted to guide different sizes of debris onto the vibrating screen belt. Once the sand and debris are on the vibrating screen belt, the debris may be collected using the same method as sifting technology.

An objective of beach cleaning strategy is to utilize the most effective method to handle pollution while considering beach erosion and changing beach terrains. As debris and pollution accumulate and beach terrain changes, it may be time consuming and difficult to monitor debris patterns. Exemplary embodiments of the present invention provide for timely and cost effective beach cleaning.

As the present invention allows for various changes and numerous embodiments, exemplary embodiments of the present invention will be illustrated in the drawings and described in detail herein. Like reference numerals may refer to like elements throughout the specification and drawings.

It will be understood that the terms "first," "second," "third," etc. are used herein to distinguish one element or location from another and the elements or locations are not limited by these terms.

Figure 1:
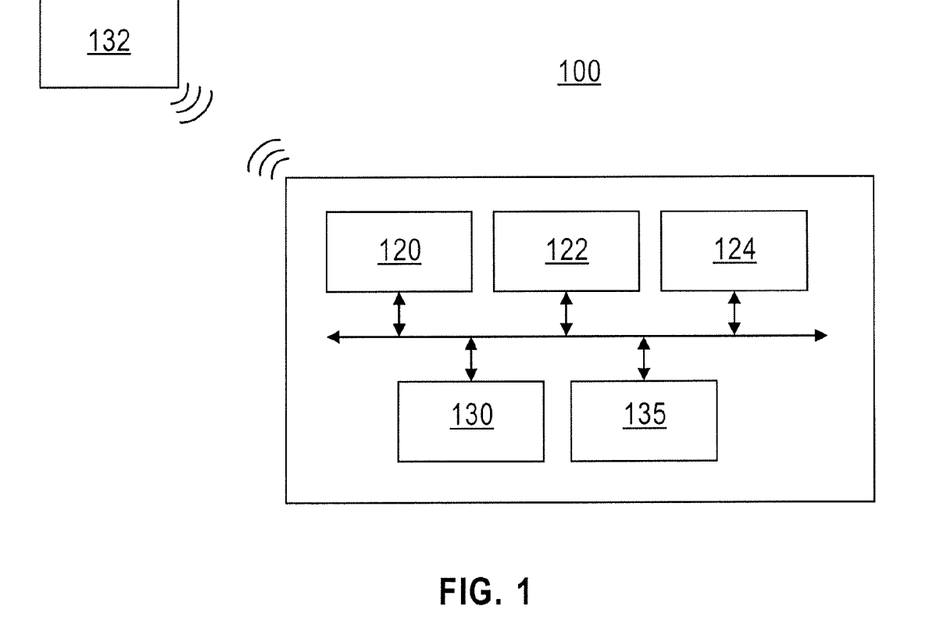
FIG. 1 is a block diagram illustrating components of a sand cleaning vehicle according to an exemplary embodiment of the present invention.
Figure 2:
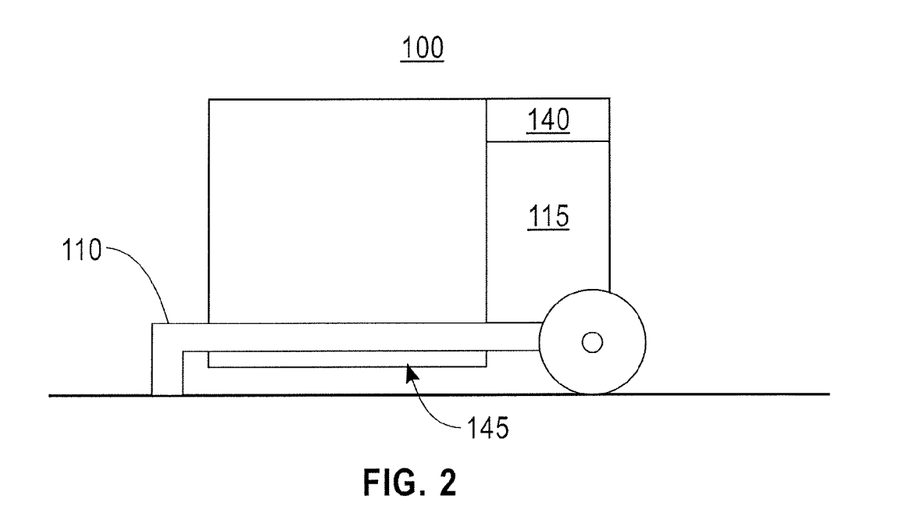
FIG. 2 illustrates a sand cleaning vehicle according to an exemplary embodiment of the present invention.

FIG. 1 is a block diagram illustrating components of a sand cleaning vehicle according to an exemplary embodiment of the present invention. FIG. 2 illustrates a sand cleaning vehicle according to an exemplary embodiment of the present invention. Some or all of the components shown in FIGS. 1 and 2 may be included in the sand cleaning vehicle according to an exemplary embodiment of the present invention.

Referring to FIGS. 1 and 2, exemplary embodiments of the present invention provide a sand cleaning vehicle 100 including a debris collection mechanism 110 that collects debris from sand, a storage compartment 115 that stores the collected debris, a capture device 120 that captures at least one image or video feed of the collected debris, a memory 122 storing a computer program, and a processor 124 that executes the computer program, in which the computer program categorizes the collected debris into a plurality of different debris types using the at least one image or video feed of collected debris. The at least one image may be a single still image. The at least one image may also be one of a plurality of consecutive images that form a video feed, The video feed may include the at least one image. The video feed may also include a plurality of consecutive images which may include the at least one image.

The sand cleaning vehicle 100 may further include a network adapter 130 that establishes a network connection with a remote computer 132, a global positioning system (GPS) device 135 that detects the current location of the sand cleaning vehicle 100, a sorting mechanism 140 that sorts the collected debris, and a disinfecting mechanism 145.

The sand cleaning vehicle 100 may use raking technology, sifting technology, or a combination of raking and sifting technology. The sand cleaning vehicle 100 may be autonomous and may be used on a plurality of surfaces including beaches, golf bunkers, resorts, playgrounds or backyards. The sand cleaning vehicle 100 may be used to comply with local environmental ordinances (e.g., if turtle eggs are present during a certain season, the sand cleaning vehicle 100 may only be allowed to clean below the surface at a depth to provide adequate distance between the sand cleaning vehicle 100 and the buried turtle eggs). The sand cleaning vehicle 100 may also be used privately or publically based on subscription-based services. A smart electronic calendar may be used by the sand cleaning vehicle 100 to schedule service delivery, as described further below.

The debris collected by the debris collection mechanism 110 may be any of coagulated oil, syringes, fish, small pebbles, shards of glass, cigarette butts, weapons, litter, tar balls, tree bark, needles, animal waste, zebra mussel shells, bottle caps, seaweed, cans, plastic, can pop-tops, but is not limited thereto.

The network adapter 130 may establish a net work connection with a remote computer 132, which is located remotely relative to the sand cleaning vehicle 100. The computer program may transmit the at least one image of the collected debris via the network adapter 130 to the remote computer 132. The computer program may also categorize the collected debris into the plurality of different debris types using debris classification models (e.g., machine learning models trained using historical or longitudinal debris data) received from the network adapter 130 from the remote computer 132. The debris classification may be based on the result of real-time visual analytics and/or deep neural nets of the debris. The analysis may be based on other aspects of the debris such as texture, sound, odors, and weight as the debris sifts may be considered, but the aspects considered are not limited thereto. Furthermore, a video or remote operator may allow experts or a crowd to do a real-time inspection, estimation, alerting, and/or classification of the collected debris. Social networking may also be used in classifying the debris.

The computer program may also generate an assessment report indicating the different debris types collected from the sand. The computer program may transmit the assessment report to the remote computer 132. The assessment report may be sent to the authorities (e.g., to a remote computer belonging to or in communication with the authorities) including, but not limited to, local government, local environmentalists, such as the Environmental Protection Agency (EPA) (e.g., for oil), health agencies (e.g., for syringes), or marine authorities (e.g., for fish).

The GPS device 135 may detect a current location of the sand cleaning vehicle 100. The computer program may use this information to create a map. The map may indicate locations at which the collected debris were collected using the at least one image of the collected debris and the current location of the sand cleaning vehicle 100. The computer program may transmit the map to the remote computer 132 via the network adapter 130.

For example, the sand cleaning vehicle 100 may travel down a beach and collect a first piece of debris at a first current location. After col lection of the first piece of debris, the sand cleaning vehicle 100 may travel to collect a second piece of debris at a second current location. A map may be created indicating the types of debris located at the different locations, which were current locations of the sand cleaning vehicle 100 when the debris was collected. A map may also be created indicating the different types of debris found in different locations. For example, dead fish may be found and concentrated in an area of the beach, which may indicate information about tides, whereas bottle caps and cans may be found in another area of the beach, which may indicate frequent use by beach goers and occurrences of parties. A dangerous area of the beach may also be mapped by the amount of hazardous debris found, such as syringes.

The map indicating the locations of the debris may be used to guide a machine operator, agencies, or an autonomous sand cleaning vehicle 100 to the areas for clean up or forecast locations of concern for future cleaning. An autonomous sand cleaning vehicle 100 may drive to the locations of concern for cleaning. Furthermore, a learning process may be used by the sand cleaning vehicles 100 to facilitate learning of environmental patterns and other factors contributing to the debris. Therefore, the sand cleaning vehicle 100 may devote additional time and resources to regions more likely to be polluted with debris based on several factors, which may include, for example, nearness to the water, tide schedules, slope of the beach, and locations. In combination with the use of a debris categorization method, such as deep neural nets, a learning process may estimate the substances the debris corresponds to (e.g., bottles, cigarette butts, etc.) with the debris spatial extent or using machine vision technology. Based on such learning processes, the sand cleaning vehicle 100 may provide guidance as to a particular cleaning method and pattern. For example, guidance may be provided to either a human operator, environmental agency, or to a navigation system of the sand cleaning vehicle 100.

The sand cleaning vehicle 100 may include a GPS device 135 and a network adapter 130. The GPS device 135 may detect a current location of the sand cleaning vehicle 100. The network adapter 130 may establish a network connection with a remote computer 132.

The computer program may track the current location of the sand cleaning vehicle 100 during at least one sand cleaning outing. The computer program may identify a high tide line on a beach during the at least one sand cleaning outing. The high tide line may correspond to a continuous physical marking identified by the capture device that indicates a portion of the beach furthest from the ocean that may be reached by a rising tide. The high tide line may be determined from databases of information from other sources. Alternatively, the high tide line may be measured by, for example, a line of oil or scum along shore objects, a substantially continuous deposit of fine shell or debris on the foreshore or berm, other physical markings or characteristics, vegetation lines, tidal gages, or other suitable means that delineate the general height reached by a rising tide; however, embodiments of the present invention are not limited thereto. The high tide line may encompass spring high tides and other high tides that may occur with periodic frequency, but may not include storm surges in which there is a departure from the predicted reach of the tide due to the piling up of water against the coast by strong winds such as those accompanying a storm. The computer program may record the locations at which each piece of the collected debris is collected. The computer program may also record the locations corresponding to the high tide line. The computer program may determine a relationship between the locations at which each piece of the collected debris is collected and the locations corresponding to the high tide line. Accordingly, the debris may have a distance and frequencies of occurrence relationship with the low high tide lines and high tide lines or a region of sand with a particular beach slope. For example, the computer program may determine that tar balls may be more likely to be located where the slope of the beach is at about a 20 degree angle in the winter and at about a 25 degree angle in the summer and may often be located about 5 feet from the high tide line in the summer. A report may be transmitted to the remote computer 132 via the network adapter 130. The report may indicate the determined relationship.

The computer program may track the current location of the sand cleaning vehicle 100 during at least one sand cleaning outing. The computer program may determine the slope of a beach at a first plurality of locations during the at least one sand cleaning outing. The slope of the beach may be determined from databases of information from other sources. Alternatively, the slope of the beach may be determined by, for example, laser-based ranging with inertial and global positioning system (GPS)-based navigation; however, embodiments of the present invention are not limited thereto. The computer program may further record the first plurality of locations and the corresponding slope, and a second plurality of locations at which each piece of the collected debris was collected. The computer program may determine a relationship between the slope of the beach and the second plurality of locations at which each piece of the collected debris was collected. Accordingly, the debris may have a distance and frequencies of occurrence relationship with the low and high tide lines or a region of sand with a particular beach slope. For example, the computer program may determine that tar balls may be more likely to be located where the slope of the beach is at about a 20 degree angle in the winter and about a 25 degree angle in the summer and may be often located about 5 feet from the high tide line in the summer. A report may be transmitted to the remote computer 132 via the network adapter 130. The report may indicate the determined relationship.

The computer program may track the current location of the sand cleaning vehicle 100 during a plurality of sand cleaning outings as the sand cleaning vehicle 100 collects debris from the sand. The computer program may create a map indicating locations in which each piece of the collected debris was collected. The computer program may further determine an environmental pattern of debris accrual using the map. The environmental pattern of debris may indicate that an area having a high debris accrual rate corresponds to at least one location in close proximity to sea, high sea tides, or a high beach slope; however, exemplary embodiments of the present invention are not limited thereto. The computer program may transmit a report indicating the environmental pattern of debris to the remote computer 132 via the network adapter 130. The report may include a map with the locations of the collected debris highlighted, latitude and longitude coordinates, or a distance from a location and cardinal direction.

The computer program may track the current location of the sand cleaning vehicle 100 during a plurality of sand cleaning outings as the sand cleaning vehicle 100 collects the debris from the sand. The computer program may record locations at which each piece of the collected debris was collected during each sand cleaning outing. Using the recorded locations, the computer program may further identify an area as having a high debris accrual rate and an area having a low debris accrual rate. The computer program may transmit a report to the remote computer 132 via the network adapter 130. The report may indicate a location of the area having the high debris accrual rate and a location of the area having the low debris accrual rate. The report may include a map with the locations of the collected debris highlighted, latitude and longitude coordinates, or a distance from a location and cardinal direction.

A current location of the sand cleaning vehicle 100 may be tracked during at least one sand cleaning outing. A high tide line may be identified on a beach during the at least one sand cleaning outing. The high tide line may correspond to a continuous physical marking identified by the capture device that indicates a portion of the beach furthest from the ocean that is reachable by a rising tide. The high tide line may be determined from databases of Information from other sources. Alternatively, the high tide line may be measured by a line of oil or scum along shore objects, a substantially continuous deposit of fine shell or debris on the foreshore or berm, other physical markings or characteristics, vegetation lines, tidal gages, or other suitable means that delineate the general height reached by a rising tide; however, embodiments of the present invention are not limited thereto. The high tide line may encompass spring high tides and other high tides that may occur with periodic frequency, but may not include storm surges in which there is a departure from the predicted reach of the tide due to the piling up of water against the coast by strong winds such as those accompanying a storm. Locations at which each piece of the collected debris is collected and locations corresponding to the high tide line may be recorded. A relationship may be determined between the locations at which each piece of the collected debris is collected and locations corresponding to the high tide line. Accordingly, the debris may have a distance and frequencies of occurrence relationship with the low and high tide lines or a region of sand with a particular beach slope. For example, the computer program may determine that tar balls may be more likely to be located where the slope of the beach is at about a 20 degree angle in the winter and about a 2.5 degree angle in the summer, and may often be located about 5 feet from the high tide line in the summer. Future sand cleaning outings may be scheduled such that the sand cleaning vehicle 100 spends more time cleaning areas having a high debris accrual rate as indicated by the determined relationship than cleaning areas having a low debris accrual rate as indicated by the determined relationship during the future sand cleaning outing.

A current location of the sand cleaning vehicle 100 may be tracked during at least one sand cleaning outing. A slope of a beach may be determined at a first plurality of locations during the at least one sand cleaning outing. The slope of the beach may be determined from databases of information from other sources. Alternatively, the slope of the beach may be determined by, for example, laser-based ranging with inertial and global positioning system (GPS)-based navigation; however, embodiments of the present invention are not limited thereto. The first plurality of locations and the corresponding slope, and a second plurality of locations at which each piece of the collected debris is collected may be recorded. A relationship between the slope of the beach and the second plurality of locations at which each piece of the collected debris was collected may be determined. Accordingly, the debris may have a distance and frequencies of occurrence relationship with the low and high tide lines or a region of sand with a particular beach slope. For example, the computer program may determine that tar halls may be more likely to be located where the slope of the beach is at about a 20 degree angle in the winter and about a 25 degree angle in the summer, and may often be located 5 feet from the high tide line in the summer. A future sand cleaning outing may be scheduled such that the sand cleaning vehicle 100 spends more time cleaning areas having a high debris accrual rate as indicated by the determined relationship than cleaning areas having a low debris accrual rate as indicated by the determined relationship during the future sand cleaning outing.

The assessment report may use weather information, such as wind and rain forecasts, to determine a risk of debris accumulation or to forecast locations of debris concerns in the future. Measurements of the categorization of the debris types may indicate total amounts and the different types of debris in a certain location, e.g., a particular beach. If such measurements are repeated over time at different times of the year, variations will be shown. The sand cleaning vehicle 100 may track debris according to groups of specific types of debris. For example, Group 1 may include debris that came from the water (e.g., fishing floats, plastic); Group 2 may include debris from beach patrons or nearby communities (e.g., cigarettes, styrofoam containers); Group 3 may include debris from floods or heavy rain (e.g., tsunami or earthquake); and Group 4 may include debris from sewage pipes or canals underneath the beach, which are taking the sewage into the deep ocean.

An interactive interface (e.g., dashboard) may be integrated with the system to provide a summarized view or information about the collected debris, such as inferred risk. Inferred risk may include information based on the concentrated presence of hazardous materials, such as toxic debris. Inferred risk may include considerations such as health risk problems. For example, a certain type of syringes may imply a risk of disease contraction, such as human immunodeficiency virus infection and acquired immune deficiency syndrome (HIV/AIDS) or hepatitis. Additionally, tar balls may include high levels of a bacterium. *Vibrio vulnificus*. Inferred risk may also include considerations such as ecological and environmental risk, such as risk to wildlife including shorebirds and fish. For example, shorebirds may suffer lead poisoning when swallowing small lead fishing weights. Furthermore, plastic may harm sea turtles and birds due to ingestion or entanglement. The sand cleaning vehicle may not need to determine the such risk entities are present, but that the inferred risks are possible given the type of debris collected (e.g., syringes and tar balls may include an inherent risk due to their characteristics and presences). Users or an operator may interact with the system to provide more context and input to the embedded processing unit.

A plurality of sand cleaning vehicles 100 may be used to collaboratively engage in cleaning and may work in concert with humans cleaning beaches in order to augment cleaning efforts. This may be used, for example, after a beach party, which may result in uncharacteristically high rates of debris disposal on the beach. The debris may include broken glass or other undesirable objects that may be dangerous to humans and wildlife. An electronic calendar of events and holidays may aid the sand cleaning vehicles 100 in efficient and timely cleaning of the beach. The electronic calendar may be synced to weather forecasts, routinely scheduled events (e.g. annual concerts and festivals), and previous information indicating trends in debris accumulation. As such, the electronic calendar may be used to schedule cleaning in response to known patterns and probability of pollution of the beaches.

Future sand cleaning outings may be scheduled such that the sand cleaning vehicle spends more time cleaning an area having a high debris accrual rate than cleaning an area having a low debris accrual rate. An area with a high debris accrual rate or an area with a low debris accrual rate may be indicated by the environmental pattern determined by using the map created by the computer program. The environmental pattern of debris may indicate that an area having the high debris accrual rate corresponds to at least one of a location in close proximity to sea, a location in close proximity to high sea tides, and a location in close proximity to high beach slope. A high debris accrual rate may indicate a high number of debris collected in a defined area over a period of time. A low debris accrual rate may indicate a low number of debris collected in a defined area over a period of time. A high debris accrual rate and a low debris accrual rate may be relative to each other in the area being cleaned by the sand cleaning vehicle 100.

Scheduling future sand cleaning outings such that the sand cleaning vehicle spends more time cleaning the area having the high debris accrual rate than cleaning the area having the low debris accrual rate during a future sand cleaning outing may be performed in an autonomous and non-autonomous circumstance. For example, when the sand cleaning vehicle 100 is autonomous, a route may be uploaded to the sand cleaning vehicle 100 and the vehicle may autonomously follow the route. The route may make the sand cleaning vehicle 100 spend more time in a location with a high debris accrual rate. When the sand cleaning vehicle 100 is non-autonomous and includes the interactive interface (e.g., display), the Interactive interface may display route instructions to a driver of the sand cleaning vehicle 100.

Furthermore, the scheduling of future sand cleaning outings may be performed by the remote computer 132 after the sand cleaning vehicle 100 provides information regarding a previous sand cleaning outing. For example, the sand cleaning vehicle 100 may send the remote computer 132 a report identifying the areas and the remote computer 132 does the scheduling.

The sand cleaning vehicle 100 may also be equipped with one or more metal detectors and other sensors, which may allow the sand cleaning vehicle 100 and system to better identify or characterize harmful objects, even underneath the sand and therefore employ techniques to extract the hazardous materials. For example, the sand cleaning vehicle 100 may employ electronic calendar feeds and metal detectors to better forecast, locate, characterize, and sort debris on the beaches. In an exemplary embodiment of the present invention, an embedded component may be included in the sand cleaning vehicle 100 to separate the debris based on types, characteristics, risk (e.g., hazardous risk), or other factors. The separation process may be based on analytics, risk analysis, and context information, such as weather. Based on such information, the sand cleaning vehicle 100 may take amelioration action (e.g., alert authorities). Depending on the type and characteristics of the debris and analysis, the sand cleaning vehicle 100 may apply or spray environmentally-safe solutions on the debris to destabilize or reduce the toxicity of the debris.

As debris types are categorized as hazardous, the disinfecting mechanism 145 may disinfect the sand in a location at which the debris categorized as hazardous debris is collected. The disinfecting mechanism 145 may include one of an ultraviolet (UV) light disinfecting mechanism that irradiates the sand with UV light or a disinfectant spraying mechanism that sprays the sand with a disinfectant spray. Additionally, the sifting of the sand may be intensive as to allow sufficient aeration of the sand. Thus, UV rays of the sun may dry and sanitize the sand. The sand may be disinfected by the disinfecting mechanism 145 while it is located within the sand cleaning vehicle 100. The sand may also be disinfected by the disinfecting mechanism 145 while it is located on the ground below the sand cleaning vehicle 100.

The assessment report may be sent to the remote computer 132 (e.g., at or in communication with local authorities) if significant organic material or decay is estimated (e.g., if hazardous debris is detected). For example, if the collected debris surpasses a threshold, the assessment report may be sent to the local authorities via the remote computer 132. A threshold may include a certain amount of debris collected by the sand cleaning vehicle 100 in a defined area (e.g., ten pieces of debris located in a half mile radius). The threshold may also include the level of hazardousness or toxicity of the collected debris. If the debris collected by the sand cleaning vehicle 100 surpasses the threshold, the assessment report is provided to the authorities. If the debris collected by the sand cleaning vehicle 100 is below the threshold, the assessment report is not provided to the authorities.

The storage compartment 115 may include a plurality of sub-compartments. The sorting mechanism 140 may separate the collected debris into the sub-compartments according to the different debris types. Accordingly, hazardous debris, such as syringes, may be placed in a separate compartment for proper disposal. The sorting mechanism 140 may include a robotic arm that separates the collected debris into the sub-compartments. Alternatively, the sorting mechanism 140 may include a sliding compartment including flaps that moves to the corresponding sub-compartment and releases the debris into the sub-compartment. The sorting mechanism 140 may also include pushing elements and pulling elements, such as small rakes, however, embodiments of the present invention are not limited thereto.

Figure 3:
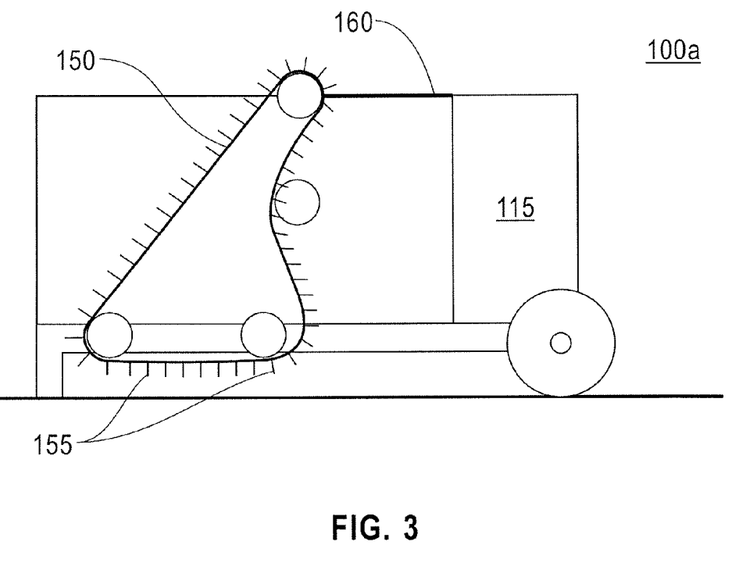
FIG. 3 illustrates a debris collection mechanism including a rotating conveyor belt and a vibrating screening belt according to an exemplary embodiment of the present invention.

FIG. 3 illustrates a debris collection mechanism including a rotating conveyor belt and a vibrating screening belt according to an exemplary embodiment of the present invention.

Referring to FIGS. 1 to 3, according to an exemplary embodiment of the present invention, the debris collection mechanism 110 may include a rotating conveyor belt 150. The rotating conveyor belt may include a plurality of tines 155 that comb the sand to collect the debris from the sand. The debris collection mechanism 110 may further include a vibrating screening belt 160, in which the rotating conveyor belt 150 deposits the collected debris and the collected sand onto the vibrating screening belt 160. The vibrating screening belt 160 may separate the collected debris from the collected sand by vibrating.

Furthermore, at least one paddle may be carried by one or more frames and configured to direct unsifted sand from the surface towards the rotating conveyor belt 150. The vibrating screening belt 160 may be configured to receive unsifted sand from the rotating conveyor belt 150, prevent debris from passing through, and allow the sand to pass through. The rotating conveyor belt 150 may consist of an endless belt including wireless mesh. The rotating conveyor belt 150 may move the debris and any adhering beach forming material towards the storage compartment 115 located at the back of the sand cleaning machine 100, 100a, 100b. Using the vibrating screening belt 160, sand may be returned to the beach and the debris may be delivered to the storage container 115.

Figure 4:
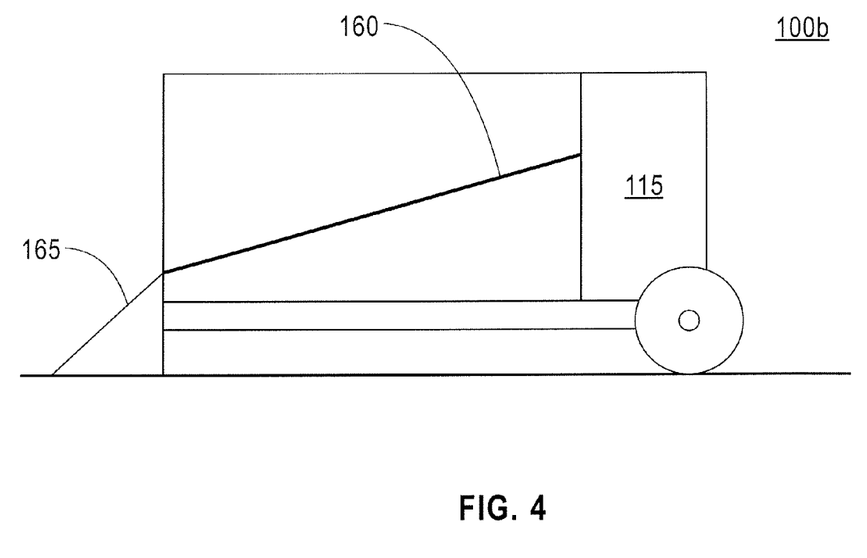
FIG. 4 illustrates a debris collection mechanism including a pick-up blade and a vibrating screening belt according to an exemplary embodiment of the present invention.

FIG. 4 illustrates a debris collection mechanism including a pick-up blade and a vibrating screening belt according to an exemplary embodiment of the present invention.

Referring to FIGS. 1, 2 and 4, according to an exemplary embodiment of the present invention, the debris collection mechanism 110 may include a pick-up blade 165 that collects the debris and a portion of the sand and a vibrating screening belt 160. The pick-up blade 165 may deposit the collected debris and the collected sand onto the vibrating screening belt 160. The vibrating screening belt 160 may separate the collected debris from the collected sand by vibrating. The pick-up blade 165 may be mounted across the chassis and project downwardly into the sand in order to lift a layer of sand. The storage compartment 115 may be, for example, a sieve, a container, a box, a bag, or a net, however, embodiments of the present invention are not limited thereto.

Figure 5:
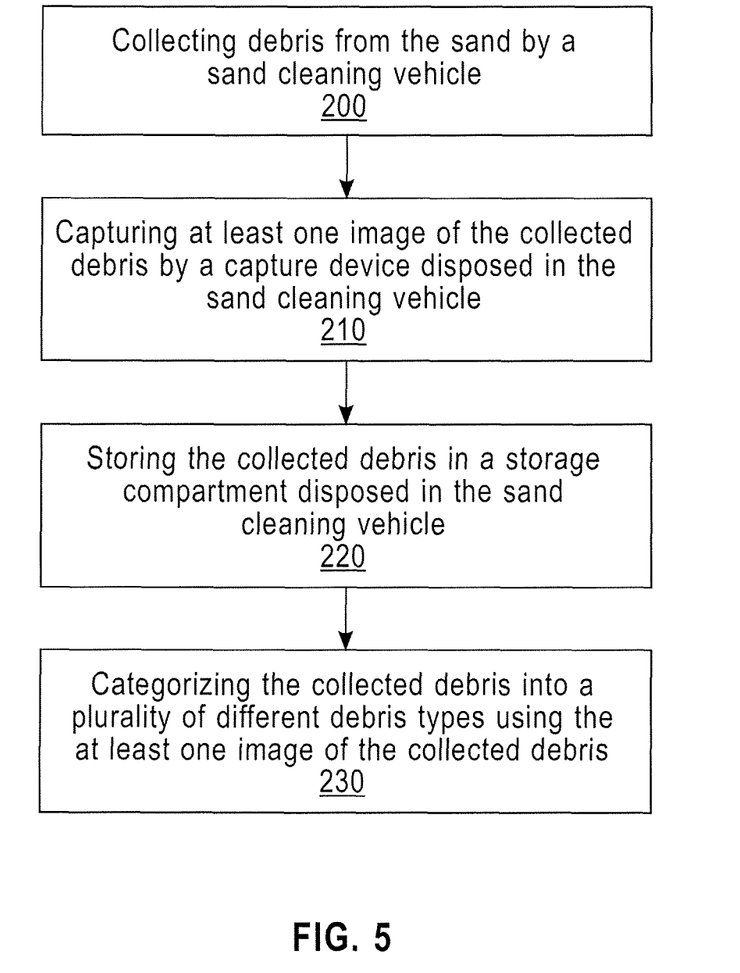
FIG. 5 is a flowchart illustrating a method of cleaning sand according to an exemplary embodiment of the present invention.

FIG. 5 is a flow chart illustrating a method of cleaning sand according to an exemplary embodiment of the present invention.

Referring to FIG. 5, according to an exemplary embodiment of the present invention, the method of cleaning sand may include collecting debris from the sand by a sand cleaning vehicle 200, capturing at least one image of the collected debris by using a capture device disposed in the sand cleaning vehicle 210, storing the collected debris in a storage compartment disposed in the sand cleaning vehicle 220, and categorizing the collected debris into a plurality of different debris types using visual analytics, deep learning, or learning models 230. Categorizing the collected debris 230 may include comparing the at least one image to a plurality of different images or video feed stored in a database. The at least one image may be matched with the plurality of images in the database, which includes images of different debris types (e.g., bottle caps, syringes, dead fish, etc.). If a match is determined, then the at least one image of the collected debris is categorized as one of the objects stored in the database. For example, similarity scores may be created using computer visual techniques. A piece of debris may be categorized based on the highest similarity score with objects stored in the database. As a piece of debris is collected and at least one image is captured by the capture device, the image will be compared with images in the database and a similarity score will be assessed (e.g., a syringe may have a higher similarity score with a stick than a bottle). Once a similarity score is determined, the highest similarity score with debris categorized in the database will be used in categorizing the debris collected by the sand cleaning vehicle 100.

The current location of the sand cleaning vehicle may be tracked as the sand cleaning vehicle collects debris from the sand. A map may be created indicating which piece of collected debris was collected at which location. Environmental patterns of debris accrual may be determined using the map. Therefore, future sand cleaning operations may be scheduled using the determined environmental patterns. The at least one image from the sand cleaning vehicle may be transmitted to at least one computer that is remotely located from the sand cleaning vehicle. The collected debris may be categorized into the plurality of different debris types by using the at least one computer. The at least one image may be transmitted from the sand cleaning vehicle to the at least one computer in real-time. An assessment report may be generated indicating the different debris types collected from the sand and the assessment report may be transmitted to at least one computer that is located remotely from the sand cleaning vehicle.

Figure 6:
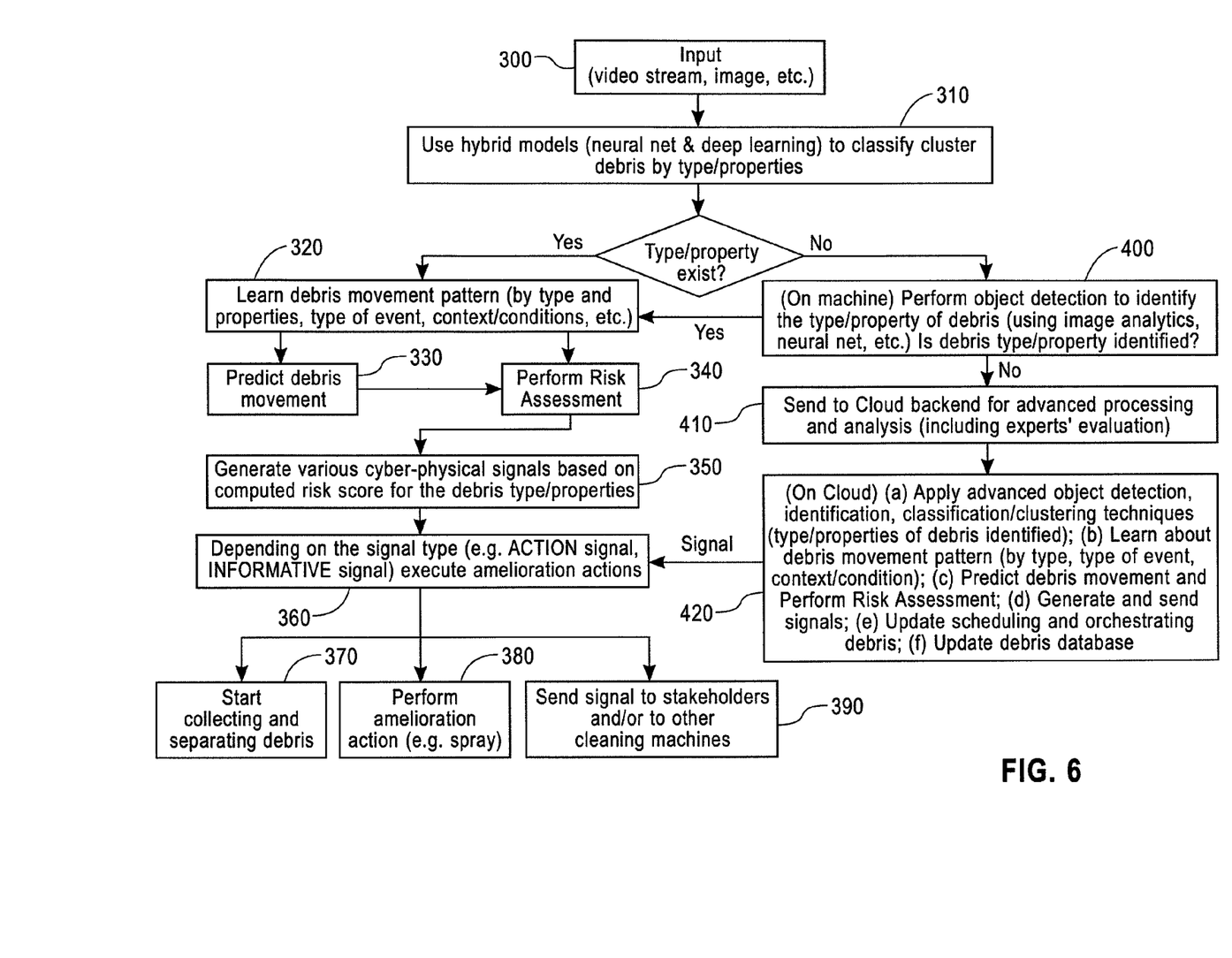
FIG. 6 is a flowchart illustrating a debris characterization and cleaning process according to an exemplary embodiment of the present invention.

FIG. 6 is a flowchart illustrating a debris characterization and cleaning process according to an exemplary embodiment of the present invention.

Referring to FIG. 6, according to an exemplary embodiment of the present invention, a debris characterization and cleaning process may include the sand cleaning vehicle receiving an input in the form of a video stream or image of the debris to be collected 300. Hybrid models, such as visual analytics, neural nets and deep learning may be used to characterize and classify a cluster of debris by type or other properties 310, which may include texture, sound, odors, and weight as the debris sifts, but are not limited thereto. If the type or property of the debris exists, the sand cleaning vehicle may learn the debris movement pattern by type and properties, such as type of event, context, conditions, etc. 320. A prediction of debris movement 330 and risk assessment 340 may be performed. Various cyber-physical signals may be generated based on a computed risk score for the debris type and properties of the debris 350. Depending on the signal type (e.g., action signal, informative signal), the sand cleaning vehicle may execute amelioration actions 360. The amelioration actions may Include, for example, collecting and separating the debris 370, performing a disinfection action in the area the debris was collected 380, and sending a signal to stakeholders and/or other sand cleaning vehicles 390.

If the type or property of the debris does not exist, the sand cleaning vehicle may perform object detection to identify the type or property of the debris (e.g., using image analytics, neural netting, etc.) 400. If the debris type or property is properly identified, the sand cleaning vehicle may learn the debris movement pattern by type and properties, such as type of event, context, conditions, etc. 320 and proceed as previously described.

If the debris type or property is not properly identified, a signal may be sent to a cloud back end for advanced processing and analysis, which may include an experts' evaluation, 410. On the cloud, advance object detection, identification, classification, and clustering techniques may be applied 420. Furthermore, the debris movement pattern may be learned and debris movement and a risk assessment may be performed 420. Signals may be generated for amelioration action and the scheduling and orchestration of debris clean up may be updated 420. Depending on the signal type (e.g., action signal, informative signal), the sand cleaning vehicle may execute amelioration actions 360, such as, for example, collecting and separating debris 370, performing a disinfection action in the area the debris was collected 380, and sending a signal to stakeholders and/or other sand cleaning vehicles 390. The debris database may be updated to include the debris type or property 420.

Figure 7:
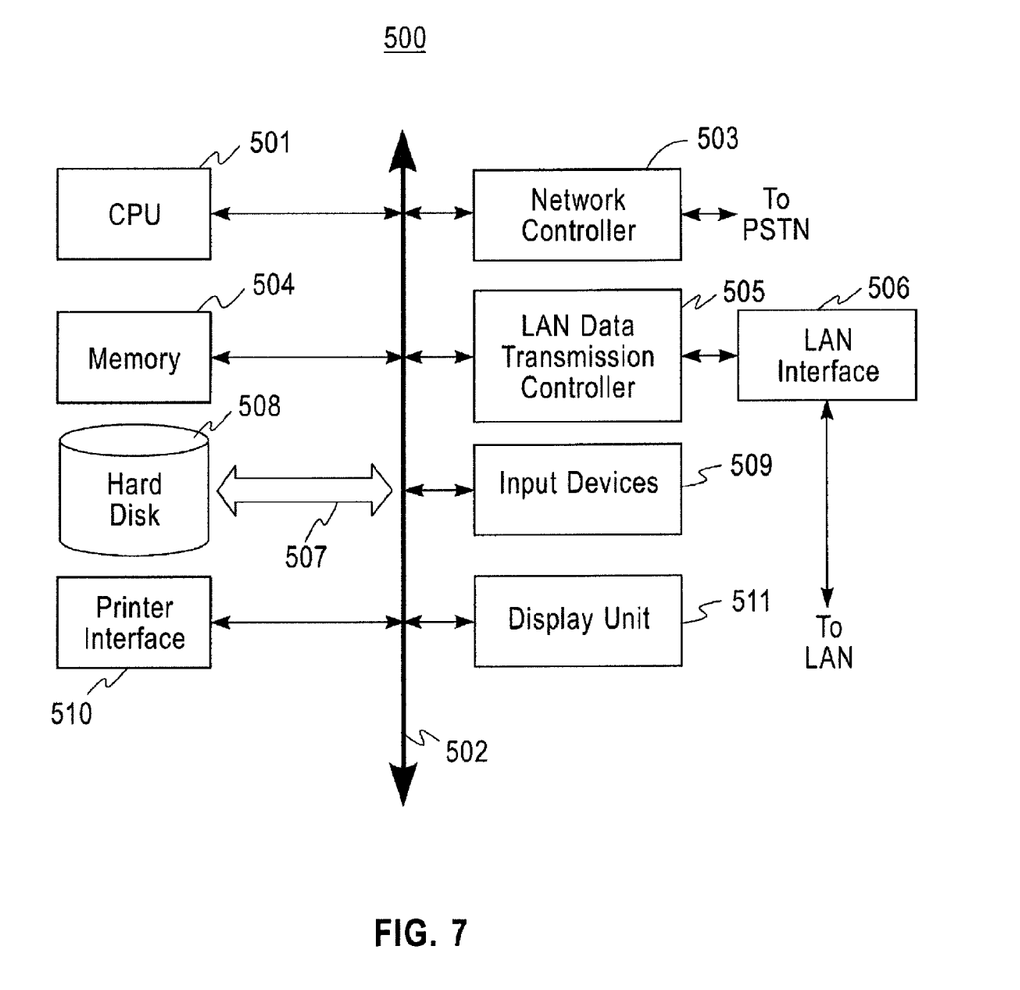
FIG. 7 illustrates an example of a computer system capable of implementing methods according to exemplary embodiments of the present invention.

FIG. 7 illustrates an example of a computer system capable of implementing the methods according to exemplary embodiments of the present invention. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

Referring to FIG. 7, the computer system referred to generally as system 500 may include, for example, a central processing unit (CPU) 501, random access memory (RAM) 504, a printer interface 510, a display unit 511, a local area network (LAN) data transmission controller 505, a LAN interface 506, a network controller 503, an internal bus 502, and one or more input devices 509, for example, a keyboard, mouse etc. As shown, the system 500 may be connected to a data storage device, for example, a hard disk, 508 via a link 507.

The descriptions of the various exemplary embodiments of the present invention have been presented for purposes of illustration, hut are not intended to be exhaustive or limited to the exemplary embodiments disclosed. Many modifications and variations will be apparent to those of ordinary skill in the art without departing from the scope and spirit of the described exemplary embodiments. The terminology used herein was chosen to best explain the principles of the exemplary embodiments, or to enable others of ordinary skill in the art to understand exemplary embodiments described herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions (see, e.g., FIGS. 1, 5-6).

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks show in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present invention has been particularly shown and described with reference to exemplary embodiments thereof, it will be understood by those of ordinary skill in the art that various changes in form and detail may be made therein without departing from the spirit and scope of the present invention as defined by the following claims.

The invention claimed is:

1. A sand cleaning vehicle, comprising:
a debris collection mechanism that collects debris from sand;
a storage compartment that stores the collected debris;
a capture device that captures at least one image of the collected debris;
a memory storing a computer program;
a processor that executes the computer program, wherein the computer program categorizes the collected debris into a plurality of different debris types using the at least one image of the collected debris,
wherein the computer program determines a pattern in locations of the collected debris;
a global positioning system (GPS) device that detects a current location of the sand cleaning vehicle; and
a network adapter that establishes a network connection with a remote computer, wherein the computer program;
tracks the current location of the sand cleaning vehicle during at least one sand cleaning outing;
identifies a high tide line on a beach during the at least one sand cleaning outing, wherein the high tide line corresponds to a continuous physical marking identified by the capture device that indicates a portion of the beach furthest from an ocean that is reached by a rising tide;
records locations at which each piece of the collected debris is collected, and location corresponding to the high tide line;
determines a relationship between the locations at which each piece of the collected debris is collected and the locations corresponding to the high tide line; and
transmits a report indicating the determined relationship to the remote computer via the network adapter.

2. The sand cleaning vehicle of claim 1,
wherein the computer program transmits the at least one image of the collected debris via the network adapter to the remote computer.

3. The sand cleaning vehicle of claim 2, wherein the computer program categorizes the collected debris into the plurality of different debris types using a debris classification model received via the network adapter from the remote computer.

4. The sand cleaning vehicle of claim 1,
wherein the computer program generates an assessment report indicating the different debris types collected from the sand, and transmits the assessment report to the remote computer.

5. The sand cleaning vehicle of claim 1, wherein the computer program creates a map indicating locations at which the collected debris were collected using the at least one image of the collected debris and the current location of the sand cleaning vehicle.

6. The sand cleaning vehicle of claim 5,
wherein the computer program transmits the map to the remote computer via the network adapter.

7. The sand cleaning vehicle of claim 1, further comprising:
a disinfecting mechanism, wherein one of the different debris types represents hazardous debris, and the disinfecting mechanism disinfects the sand at a location at which debris categorized as the hazardous debris is collected, wherein the sand is disinfected while it is located within the sand cleaning vehicle or on ground below the sand cleaning vehicle.

8. The sand cleaning vehicle of claim 7, wherein the disinfecting mechanism comprises one of an ultraviolet (UV) light disinfecting mechanism that irradiates the sand with UV light, and a disinfectant spraying mechanism that sprays the sand with a disinfectant spray.

9. A sand cleaning vehicle, comprising:
a debris collection mechanism that collects debris from sand;
a storage compartment that stores the collected debris;
a capture device that captures at least one image of the collected debris;
a memory storing a computer program;
a processor that executes the computer program, wherein the computer program categorizes the collected debris into a plurality of different debris types using the at least one image of the collected debris;
a global positioning system (GPS) device that detects a current location of the sand cleaning vehicle; and
a network adapter that establishes a network connection with a remote computer, wherein the computer program:
tracks a current location of the sand cleaning vehicle during at least one sand cleaning outing;
determines a slope of a beach at a first plurality of locations during the at least one sand cleaning outing;
records the first plurality of locations and the corresponding slope, and a second plurality of locations at which each piece of the collected debris is collected;
determines a relationship between the slope of the beach and the second plurality of locations at which each piece of the collected debris was collected; and
transmits a report indicating the determined relationship to the remote computer via the network adapter.

10. The sand cleaning vehicle of claim 1, further comprising:
a sorting mechanism that sorts the collected debris,
wherein the storage compartment comprises a plurality of sub-compartments, and the sorting mechanism separates the collected debris into the sub-compartments according to the different debris types.

11. The sand cleaning vehicle of claim 1, wherein the sand cleaning vehicle is an autonomous vehicle.

12. A method of cleaning sand, comprising:
collecting debris from the sand by a sand cleaning vehicle;
capturing at least one image of the collected debris by a capture device disposed in the sand cleaning vehicle;
storing the collected debris in a storage compartment disposed in the sand cleaning vehicle;
categorizing the collected debris into a plurality of different debris types using the at least one image of the collected debris;
determining a pattern in locations of the collected debris;
tracking a current location of the sand cleaning vehicle during at least one sand cleaning outing;
identifying a high tide line on a beach during the at least one sand cleaning outing, wherein the high tide line corresponds to a continuous physical marking identified by the capture device that indicates a portion of the beach furthest from an ocean that is reached by a rising tide;

recording locations at which each piece of the collected debris is collected, and locations corresponding to the high tide line;

determining a relationship between the locations at which each piece of the collected debris is collected and the locations corresponding to the high tide line; and scheduling a future sand cleaning outing such that the sand cleaning vehicle spends more time cleaning areas having a high debris accrual rate as indicated by the determined relationship than cleaning areas having a low debris accrual rate as indicated by the determined relationship during the future sand cleaning outing.

13. The method of claim 12, wherein categorizing the collected debris into the plurality of different debris types using the at least one image comprises:

comparing the at least one image to a plurality of images stored in a database, wherein each image stored in the database belongs to one of the different types of debris; and matching the at least one image to one of the plurality of images in the database.

14. A method of cleaning sand, comprising:

collecting debris from the sand by a sand cleaning vehicle;

capturing at least one image of collected debris capture device disposed in the sand cleaning vehicle;

storing the collected debris in a storage compartment disposed in the sand cleaning vehicle;

categorizing the collected debris into a plurality of different debris types using the at least one image of the collected debris;

determining a pattern in locations of the collected debris;

tracking a current location of the sand cleaning vehicle during at least one sand cleaning outing;

determining a slope of a beach at a first plurality of locations during the at least one sand cleaning outing;

recording the first plurality of locations and the corresponding slope, and a second plurality of locations at which each piece of the collected debris is collected;

determining a relationship between the slope of the beach and the second plurality of locations at which each piece of the collected debris was collected; and scheduling a future sand cleaning outing such that the sand cleaning vehicle spends more time cleaning areas having a high debris accrual rate as indicated by the determined relationship than cleaning areas having a low debris accrual rate as indicated by the determined relationship during the future sand cleaning outing.

15. A method of cleaning sand, comprising:

collecting debris from the sand by a sand cleaning vehicle;

capturing at least one image of the collected debris by a capture device disposed in the sand cleaning vehicle;

storing the collected debris in a storage compartment disposed in the sand cleaning vehicle;

categorizing the collected debris into a plurality of different debris types using the at least one image of the collected debris;

determining a pattern in locations of the collected debris;

tracking a current location of the sand cleaning vehicle, during a plurality of sand cleaning outings, as the sand cleaning vehicle collects the debris from the sand;

recording locations at which each piece of the collected debris was collected during each sand cleaning outing;

identifying an area having a high debris accrual rate and an area having a low debris accrual rate using the recorded locations; and scheduling a future sand cleaning outing such that the sand cleaning vehicle spends more time cleaning the area having the high debris accrual rate than cleaning the area having the low debris accrual rate during the future sand cleaning outing.

16. The method of claim 12, further comprising:

transmitting the at least one image from the sand cleaning vehicle to at least one computer that is remotely located from the sand cleaning vehicle, wherein the collected debris is categorized into the plurality of different debris types by the at least one computer.

17. The method of claim 16, wherein the at least one image is transmitted from the sand cleaning vehicle to the at least one computer in real-time.

18. The method of claim 12, further comprising:

generating an assessment report indicating the different debris types collected from the sand; and transmitting the assessment report to at least one computer that is remotely located from the sand cleaning vehicle.

* * * * *